United States Patent [19]

van den Honert et al.

[11] Patent Number: 4,535,785

[45] Date of Patent: Aug. 20, 1985

[54] METHOD AND APPARATUS FOR DETERMINING THE VIABILITY AND SURVIVAL OF SENSORI-NEUTRAL ELEMENTS WITHIN THE INNER EAR

[75] Inventors: Christopher van den Honert, St. Paul; Paul H. Stypulkowski, Vadnais Heights, both of Minn.

[73] Assignee: Minnesota Mining and Manufacturing Co., St. Paul, Minn.

[21] Appl. No.: 421,992

[22] Filed: Sep. 23, 1982

[51] Int. Cl.$^3$ .......................... A61B 5/05; A61B 5/12
[52] U.S. Cl. .................................................. 128/746
[58] Field of Search ........................ 128/746, 731–733; 73/585; 179/12

[56] References Cited

U.S. PATENT DOCUMENTS

| | | |
|---|---|---|
| 3,752,939 | 8/1973 | Bartz . |
| 3,893,450 | 7/1975 | Ertl .................................... 128/731 |
| 3,901,215 | 8/1975 | John .................................... 128/746 |
| 4,303,073 | 12/1981 | Archibald . |
| 4,305,400 | 12/1981 | Logan . |
| 4,421,122 | 12/1983 | Duffy .................................. 128/731 |

FOREIGN PATENT DOCUMENTS 2299004 8/1976 France ................................ 128/746

OTHER PUBLICATIONS

"Brain Stem Electric Response Audiometry", Ward, 6–81.
"Effects Electric Current Applied to Cochlear Partition . . . ", Teas et al., 7–69, JASA.
Honrubia et al., "Physiological Basis of Cochlear Transduction and Sensitivity," 64 *Transactions of the American Otological Society*, 21–34, (Apr. 25–26, 1976).
Sand et al., "Electrical and Mechanical Stimulation of Hair Cells: The Mudpuppy," A 102 *Journal of Comparative Physiology* 13–25, (1975).
van den Honert et al., "Generation of Unidirectionally Propogated Action Potentials in a Peripheral Nerve by Brief Stimuli," 206 *Science* 1311–1312, (Dec. 14, 1979).
van den Honert, et al., "A Technique for Collision Block of Peripheral Nerve," BME-28, No. 5, *IEEE Transactions on Biomedical Engineering*, 373–382, (May 1981).
Jones et al, "Three Mechanisms of Hearing by electrical Stimulation," 12 *Journal of the Acoustical Society of America*, 281–290, (Oct. 1940).
Moxon, "Electrical Stimulation of the Cat's Cochlea; a Study of Discharge Rates in Single Auditory Nerve Fibers," MS Grad. Thesis, *Massachusetts Institute of Technology*, 6–7, 34–36, (Sep. 1967).
Moxon, "Neural and Mechanical Responses to Electric Stimulation of the Cat's Inner Ear," Ph.D. Grad Thesis, *Massachusetts Institute of Technology* 79–89, 202–206, (Jun. 1971).
Teas et al., "Effects of Electrical Current Applied to Cochlear Partition on Discharges in Individual Auditory-Nerve Fibers," 47 *Journal of the Acoustical Society of America*, No. 6, Part 2, 1527–1537, (1970).
"Research Laboratory of Electronics Quarterly progress Report," 90 *Massachusetts Institute of Technology*, 270–275, (Jul. 15, 1968).
Konishi et al, "Effects of Electrical Current Applied to Cochlear Partition on Discharges in Individual Auditory-Nerve Fibers I, Prolonged Direct-Current Polarization," 47 *Journal of the Acoustical Society of America* No. 6, Part 2, 1519–1527, (1970).

Primary Examiner—Lee S. Cohen
Assistant Examiner—Steven Falk
Attorney, Agent, or Firm—Donald M. Sell; James A. Smith; William D. Bauer

[57] ABSTRACT

A method and apparatus for diagnosing the extent of survival of the peripheral sensori-neural elements within the inner ear of a patient by stimulating the patient with one or more pair of electrical stimulus signals having a known amplitude and inter-signal delay, and by measuring the electrical activity within the nervous system of the patient which results from these stimulus signals and comparing the activity which results from the second stimulus signal with the activity which results from the first stimulus signal.

15 Claims, 6 Drawing Figures

METHOD AND APPARATUS FOR DETERMINING THE VIABILITY AND SURVIVAL OF SENSORI-NEUTRAL ELEMENTS WITHIN THE INNER EAR

BACKGROUND OF THE INVENTION

The present invention relates to a method and apparatus for diagnosing and locating a hearing impairment within a patient, and more particularly for determining the presence, location and extent of viability of certain sensori-neural structures within the cochlea of that patient.

An ear can functionally be described as having two portions—a transducing portion which analyzes and processes the sounds or acoustic vibrations which reach it, thereby causing resultant electrical impulses to be sent to the brain; and a conducting portion which conveys the acoustic vibrations to the transducing portion. The conducting portion of the ear consists generally of the outer and middle ear, and the transducing portion consists generally of the inner ear and its connections to the auditory nerve. When a hearing impairment exists, it may be located in either or both of the perceiving and/or the conducting portions of the ear. When the outer or middle ear is impaired, the hearing impairment is described as conductive and when the inner ear or auditory nerve is impaired, the impairment is described as perceptive or "sensori-neural." If the impairment is conductive, it typically can be surgically corrected or compensated for by an amplification of the acoustic vibrations which are to be heard. Such amplification can be accomplished with conventional hearing aids. If, however, the impairment is perceptive or sensori-neural, conventional hearing aids are generally not effective, and a further determination must be made as to whether the impairment is within the inner ear, the auditory nerve, or both, and to what extent the impairment exists, before the possibility of any treatment can be predicted. The complexity of the inner ear and its connections to the auditory nerve complicate this determination.

When the inner ear is impaired, there is generally a failure within the mechanism responsible for converting the acoustic vibrations into the processed electrical signals which are then transmitted to the brain via the auditory nerve. One component of this mechanism involves tiny receptor cells within the inner ear, called hair cells, which are mechanically activated by the acoustic vibrations conducted through the middle ear. In a manner not precisely understood, the mechanically activated hair cells are caused to release a chemical messenger which travels across the junction or synapse between the haircells and the nerve fibers of the auditory nerve, to activate the nerve fibers of the auditory nerve. The nerve fibers respond by generating electrical action potentials which are then propagated toward the brain.

It is also known that the presence of an electrical signal in the vicinity of the inner ear can cause non-impaired or even partially impaired hair cells within the inner ear to vibrate. These vibrations are able to cause an electrical impulse or action potential to be generated within the auditory nerve, in a sequence analogous to that which occurs in a normally functioning ear, even though these vibrations have not been initiated in the conventional manner. This phenomena has been labelled the cochlear electrophonic effect. (See for example the work done by R. Clark Jones, et al, at Harvard University as published in the Journal of the Acoustic Society of America, Volume 12, October 1940, as well as the graduate theses prepared by Edwin C. Moxon at the Massachusetts Institute of Technology, dated September, 1967 (MS) and June, 1971 (Ph.D).

The auditory nerve fibers can also be directly stimulated by applied electrical signals, which cause these fibers to generate action potentials without going through the chemical interface or synapse between the hair cells and the auditory nerve fibers. In order for this direct stimulation of the auditory nerve to occur, the stimulus electrical signal must either be of an adequate magnitude to directly generate action potentials within the auditory nerve fibers, or alternatively, if the applied signal is subthreshold, there must be a sufficient quantity of signals in close enough time proximity to additively stimulate the auditory nerve fibers. This phenomena is also discussed in the work of Jones et al previously referenced.

Although both the cochlear electrophonic effect and the direct stimulation of the auditory nerve involve auditory stimulation with an electrical signal, they do not provide the information necessary to help the physician diagnose the extent or locality of an impairment within the inner ear.

SUMMARY OF THE INVENTION

The apparatus and method according to the present invention provides a minimally invasive auditory diagnostic procedure which attempts to identify a disfunction of the inner ear, and which also provides an indication of the activity, location and extent of viability of specific sensori-neural elements within the inner ear.

As will be described, the inventors of the present invention have found through experimentation that controlled electrical signals, in addition to directly stimulating the auditory nerve fibers, can also be used to electrically stimulate the hair cells in a manner not dependent upon the electrophonic effect, but still causing the hair cells to chemically activate the synapse with the auditory nerve. The present inventors have also determined that depending upon the magnitude of the stimulus signal and the location of the stimulus electrode, the direct electrical stimulation of the auditory nerve fibers can be broken down into two different processes in which separate portions of the auditory nerve fibers are stimulated, i.e. the peripheral denritic regions of the auditory neurons forming the nerve fibers can be stimulated, or the central axons of these neurons can also be the stimulated. Depending upon which of these sites is stimulated, different neural behavior is observed to occur. The present invention recognizes this and affords a method of analyzing the electrical response which results within the patients nervous system upon an applied electrical stimulus, to determine which of the mechanisms have contributed to the electrical response resulting from the artificial stimulation, i.e. the non-electrophonic electrical stimulation of hair cells and the chemical activation viz the synapse of the auditory nerve, or the direct electrical stimulation of the auditory nerve via either the axons or dendrites, or all three. This analysis not only provides an indication of the function or disfunction of the inner ear, but it can also provide an indication of the location of any viable sensori-neural elements within the inner ear, and the extent of their viability.

With the present invention, the inner ear of a hearing impaired patient is stimulated with a first electrical stimulation signal, and the electrical activity within the patient's nervous system which results from that first electrical stimulation signal is measured. The patient is then stimulated with a second stimulation signal, and the electrical activity within the nervous system which results from that second stimulation signal (as well as any remnant activity due to the first signal) is also measured. The electrical activity measured in these two cases are compared and the magnitude of the electrical response present in the second case is determined as a percentage of that present in the first case. This determination is made with the time delay between the two signals as a variable, because experimental results have indicated that the response resulting from the direct electrical stimulation of the auditory nerve axons, and the response generated due to the electrical stimulation of the peripheral structures such as the hair cells or the auditory nerve dendrites, can be separated through an analysis of the magnitude of the responses to the two stimulation signals, as compared with the time delay between the two stimulation signals. If the two signals are of equal magnitude and the time period between two signals is decreased, the magnitude of the electrical response elicited by the second stimulus signal will begin to follow an established characteristic pattern if the elicited response is due to the direct electrical excitation of the auditory nerve axons, such as would be the case with a totally impaired inner ear. If, however, the excitation of the auditory nerve fibers has at least partially occured indirectly through the stimulation of the peripheral structures, such as the hair cells or the dendrites, the elicited response pattern is significantly different from the characteristic pattern. Hence, this test can be used to determine the actual and observed means of nerve fiber excitation, as compared to the predicted normal response for a healthy inner ear. The manner in which the elicited response differs from the predicted healthy ear response can then be used to predict the existance and location of any contributing peripheral sensori-neural elements (dendrites and/or hair cells) within the inner ear and the extent of their viability.

DESCRIPTION OF THE ACCOMPANYING DRAWING

The present invention will be further described hereinafter with reference to the accompanying drawing wherein.

DETAILED DESCRIPTION OF THE PREFERRED EMBODIMENT

Figure 1:
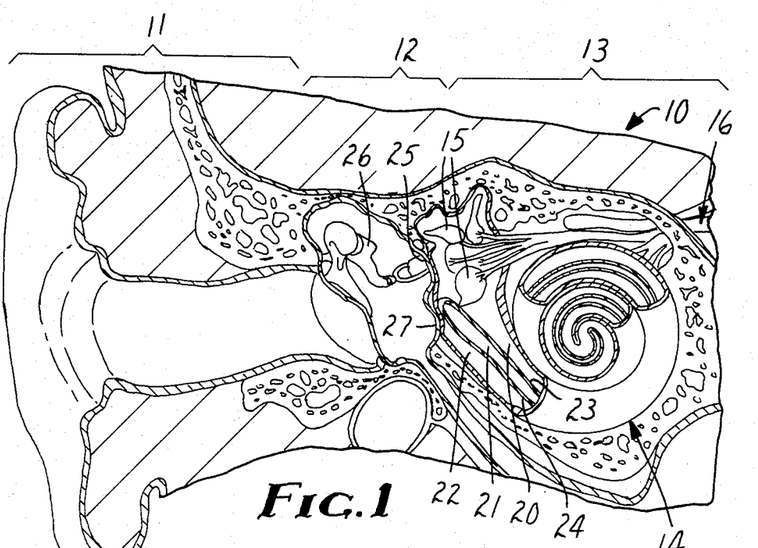
FIG. 1 is a diagram of an ear with portions cut away to reveal the structure therein.

FIG. 1 illustrates the components of an ear 10 wherein the outer ear is generally designated 11, the middle ear generally designated 12, and the inner ear generally designated 13. The inner ear 13 consists of the cochlea 14 and its connections to the auditory nerve 16, as well as the vestibular canals 15. The cochlea 14 is actually a system of three fluid filled tubes, helically coiled side by side, thus resembling a snail shell. The three tubes are known as the scala vestibuli 20, the scala media 21, and the scala tympani 22. The scala vestibuli 20 and the scala media 21 are separated from each other by a first membrane, known as Reissner's membrane 23, and the scala tympani 22 and scala media 21 are separated from each other by second membrane known as the basilar membrane 24. At the distal end of the cochlea, the scala vestibuli and the scala tympani 22 are joined together such that a fluid called perilymph, which is present within both the scala vestibuli 20 and the scala tympani 22, can freely flow from one tube to the other. At the proximate or basal end of the cochlea 14, the scala vestibuli 20 terminates in a membranous region called the oval window 25, which is in turn fastened to the ossicular bones 26 of the middle ear 12, and the basal end of the scala tympani 22 terminates in a membranous region which is known as the round window 27. The perilymph is therefore contained within the scala tympani 22 and the scala vestibuli 20.

Figure 2:
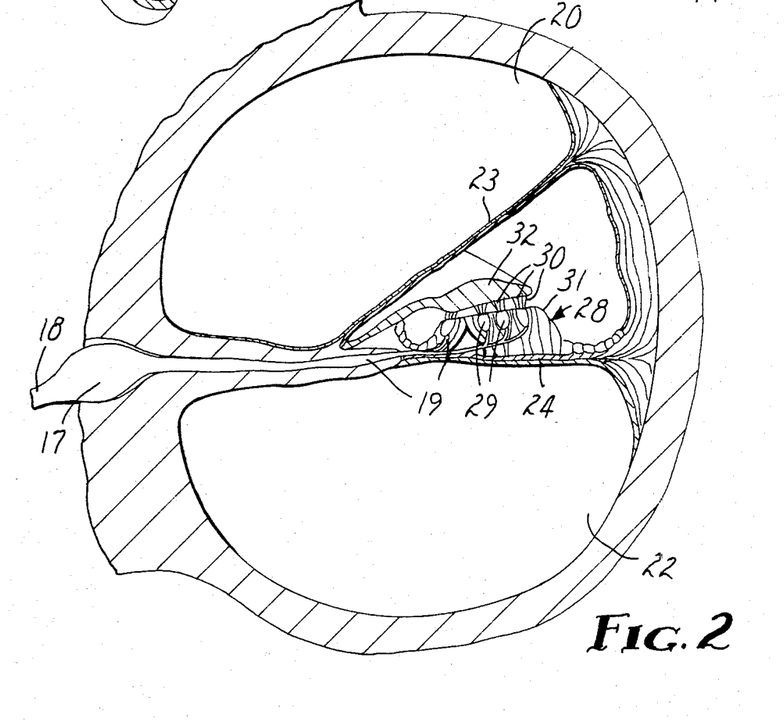
FIG. 2 is an enlarged partial sectional view of the cochlea of the ear shown in FIG. 1.

An enlarged cross section of the cochlea 14 is illustrated in FIG. 2. As can be seen the basilar membrane 24 supports a structure known as the Organ of Corti 28 which contains a series of cells, called hair cells 29, because they contain a plurality of fiber-like projections, or cilia 30 projecting from one end. The base of the hair cells 29 form synaptic connections with a network of dendritic endings of the auditory neurons. The upper ends of the hair cells are fixed tightly in a structure called the reticular lamina 31, which is a rigid structure ultimately secured to the basilar membrane 24. A gelatinous membrane called the tectorial membrane 32, extends from the juncture between the scala media 21 and the scala vestibuli 20. The tectorial membrane 32 is not secured to the basilar membrane 24, but is rather isolated from any movement of the basilar membrane 24. This tectorial membrane 32 is positioned such that it contacts the distal tips of the cilia 30. The individual auditory neurons are composed of three major subdivisions, spiral ganglion cells or cell bodies 17 located in the bony area protecting the inner ear 13, central axons 18 which normally carries information, in the form of electrical pulses, toward the brain, and a peripheral dendrites 19 which receives chemical messages from the hair cells 29 and transforms these messages into the electrical pulses carried by the axons 18.

In a functioning ear, acoustic vibrations are transmitted through the ossicular bones 26 of the middle ear to the oval window 25, causing the oval window 25 to vibrate at a rate dependant upon the frequency spectrum of the applied acoustic energy. The movement of the oval window 25 causes a flow or movement of the perilymph within the scala vestibuli 20. This movement is in turn transmitted through the scala tympani 22 to the round window 27, which causes the round window 27 to bulge out in an opposite phase to that of the oval window 25. This movement of the perilymph imposed by the vibrations of the oval window 25 causes the basilar membrane 24 to vibrate in a corresponding fashion. This vibration of the basilar membrane 24 relative to the tectorial membrane 32 creates a shearing force on the cilia 30, which results in a bending of the cilia 30. In a manner not thoroughly understood, this bending of the cilia 30 generates a change in the electrical potential across the outer membrane of the hair cell 29, which causes a release of a chemical messenger, known as a neurotransmitter, from the hair cell 29. The neuro transmitter diffuses across the synapse between each of the hair cells 29 and their corresponding dendrites 19, (the pre- and postsynaptic cells respectively). Upon reaching the dendrites 19, the transmitter molecules are believed to chemically bind with specific protein molecules, known as receptors, which are located on the dendrites 19. The chemical binding of the transmitter molecules to the receptor molecules causes a permeability change in the postsynaptic cell membrane, which results in the flow of an ionic current across the membrane, and which produces a localized potential change across the outer membrane of the postsynaptic or auditory nerve cell. If this potential change across the postsynaptic cell membrane is of sufficient magnitude, the postsynaptic cell initiates a regenerative process of localized ionic current flow, known as an action potential. This action potential propagates along the entire length of the auditory neuron as a local depolarization of the membrane. In this manner, changes in the membrane potential of the hair cell 29 induced by mechanical (acoustic) vibrations, can lead to the generation of action potentials in the auditory nerve fibers which will propagate toward the brain.

Direct electrical stimulation of the cochlea is also known and has been previously performed. The site of excitation has however been unknown, and just assumed to be somewhere on the auditory nerve cell. Any effects, however, of the electrical stimulation on the hair cell was presumed to be limited to the "electrophonic" effect previously mentioned. The present invention is based upon the finding that (a) hair cells can also be directly stimulated by electrical currents, in a manner not involving the electrophonic effect, and caused to excite the auditory nerve fibers via the chemical synaptic transmission process that has already been discussed herein, and that (b) auditory neurons can be directly stimulated with the site of excitation being either at some point along the dendritic processes 19, i.e., distal to the axons 18 and the spiral ganglion 17; as well as directly at the axons. Evidence supporting this discovery has been obtained using the methods and criteria which will now be discussed.

Nerve membranes exhibit a property following the production of an action potential known as refractoriness. That is to say, for a short period of time following the generation of a single action potential in a single nerve axon, a second action potential cannot be elicited, even with increased stimulus strength. This period of time, called the "absolute refractory period", has been experimentally determined to be approximately 300 microseconds in the axons of the auditory nerve fibers of a cat. A similar absolute refractory period is also expected in humans. Following the absolute refractory period there is a slightly longer period of time during which a second action potential can be generated only with an increased stimulus intensity. This longer period is called the "relative refractory period".

Figure 4:
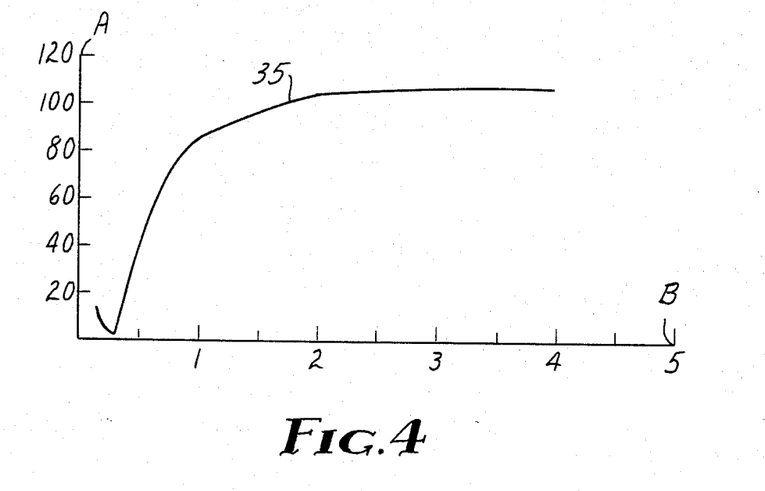
FIGS. 4 and 5 are graphs of expressed monitored electrical responses obtained by the present invention as a function of the time interval between pulses.

If two successive electrical stimuli are applied to a whole nerve, such as the auditory nerve 16 (which is composed of a population of single nerve fibers), and the interval between the two stimuli is systematically varied, a relationship between the compound action potential amplitude (the measurable summed activity of the excited population of nerve fibers) elicited by the second stimulus and the interpulse interval (IPI) can be determined. As the two stimuli are moved closer together in time, such that an IPI of 300 micro seconds is approached, more and more axons should enter their refractory period and fail to generate action potentials in response to the second stimulus. The amplitude of the second compound action potential should therefore gradually decrease to zero. FIG. 4 shows this dependence for an antidromically (i.e., the signal is applied to the nerve at the opposite end from which it would normally occur) stimulated auditory nerve in an experimental animal. In this case the stimulus acts only upon the axons because the stimulating electrode is placed at the central termination of the auditory nerve in the brainstem. In order to normalize the response elicited by the second stimulus, the units along the ordinate axis "A" of FIG. 4 express the magnitude of the response due to the second stimulus as a percentage of the response elicited by the first stimulus. The units along the abscissa "B" express the IPI in milliseconds. The resulting response pattern 35 exhibits the characteristic montonic decline as the interpulse interval is decreased, such as would be consistant with axonal refractoriness, as described above. As can be seen there is a relatively large response at 1.5 milliseconds IPI with a monotonic decrease in the response as the IPI decreases to 0.3 milliseconds.

This relationship between the interpulse delay and neuronal response with direct electrical stimulation is observed to be greatly modified if the excitation of the nerve fibers is known to occur at least partially through the previously described peripheral mechanisms. For example:

(1) Electrical stimuli applied to the cochlea will often produce a compound action potential response (as measured at the intracranial portion of the auditory nerve) that consists of two or three interacting components. These components differ in their response latency, in a manner which appears to be dependent upon the amplitude of the stimulus signal. The longest latency component, for example, occurs at the lowest stimulus amplitudes and the shortest latency component occurs in response to the highest stimulus amplitudes.

(2) A significant delay occurs in the response latency of the later components of the compound action potential (as measured at the intracranial portion of the cochlear nerve) for an electrical stimuli applied to the cochlea in the orthodromic or normal direction of conduction, as compared to the response latency measured for transmission in the opposite direction (antidromic conduction). Since it is known that axons conduct impulses at equal speeds in both directions, the increased response latency in the orthodromic direction implies an increased conduction length or the presence of a propagation delay in the transmission line such as would occur due to the intervention of the spiral ganglion cell or the presence of a synapse. In addition the latency of the earliest component approximates the latency of an antidromically evoked response, implying that it reflects direct activation of the central axonal portion of the auditory nerve and therefore independent of the peripherally mediated response.

(3) Electrical stimuli applied to the cochlea in rapid succession demonstrate that the later responses do not follow the known pattern attributable to axonal refractoriness while the earliest response, like an antidromically evoked response, does.

(4) Recordings from individual auditory neurons which are activated by electrical stimulation have also demonstrated three distinct stimulus amplitude dependent response patterns, which patterns are independent of the electrophonic effect, and which patterns correspond to the components seen in the compound recordings from the whole auditory nerve.

(5) Electrical stimulation applied to a cochlea in which the peripheral sensori-neural elements have been surgically removed has demonstrated that only the early response is evident and that the refractory behavior which is observed is characteristic of the expected behavior for electrically stimulated axons.

(6) As has been discussed, an auditory nerve fiber is incapable of responding twice within a time interval of approximately 0.3 ms. Therefore, if a second stimulus is delivered less than 0.3 ms after the first, any additional compound response which it elicits must represent activity in fibers which were not activated by the first stimulus (being too far from the electrode) but which required two closely spaced stimuli in order achieve threshold. These axons are only subliminally excited by the first stimulus. The additive effect of the two stimuli is known as temporal summation. Using antidromic stimulation it has been demonstrated that auditory nerve axons do not exhibit temporal summation unless the stimuli are less than 0.3 ms apart. In contrast orthodromic stimulation through a cochlear electrode can produce temporal summation of the late response with inter-stimulus intervals (IPI's) of up to 0.75 ms. The subliminal excitation must therefore be more prolonged at the peripheral sensorineural structures than at the axonal membrane. This occurs in both normal animals and those animals whose hair cells have been destroyed.

Figure 5:
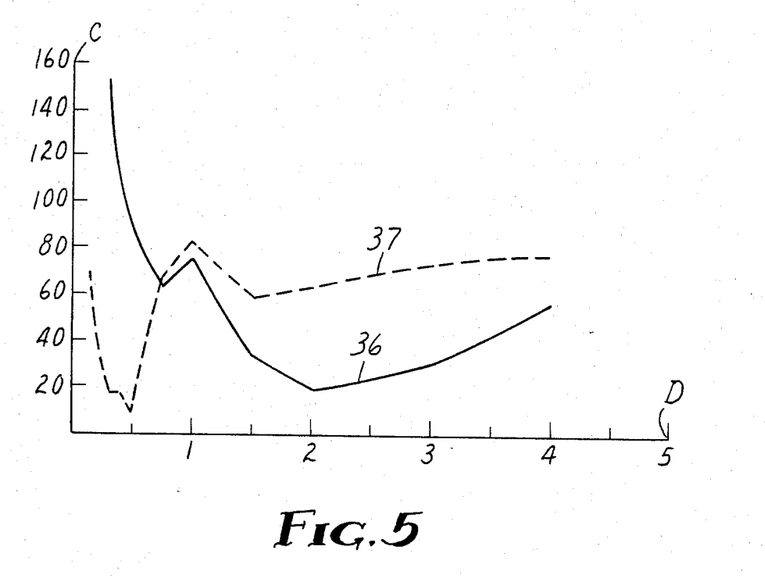

FIG. 5 shows two types of normalized evoked responses which are known to be heavily dominated by auditory nerve fibers activated via one or both of the peripherally mediated mechanisms. Again, the ordinate "C" expresses the magnitude of the response due to the second stimulus as a percentage of the response elicited by the first stimulus, and the abscissa "D" expresses the IPI in milliseconds. Two types of responses are shown. The response indicated by the solid line 36 is that which typically results from low stimulus amplitudes while the response indicated by the dashed line 37 is that which typically results from high stimulus amplitudes. As can be seen, both response patterns do not appear to be dominated by the refractoriness of the axons and therefore the characteristic montonic decline is not present. Rather other physiological phenomena appear to dominate, indicating such effects as a decrease in the efficiency of the synaptic transmission or a failure of an action potential to propagate across the cell body. This behavior appears regardless of whether or not the hair cells are intact, i.e., the same response patterns have been measured in animals whose hair cells have been totally eliminated by prior administration of an ototxic drug. The resulting differences in the neuronal response pattern to closely spaced stimuli as shown by comparing FIGS. 4 and 5 demonstrate that it is possible to discern the mechanism of activation of the auditory neurons by the obtained response pattern, and thereby determine the presence and viability of any peripheral sensorineural elements of the cochlea which are contributing to the resulting response.

Based upon the nature of these observed phenomena and the differences which occur, a method and apparatus has been developed for electrophysiologically assessing the presence and viability of these peripheral sensorineural elements within the cochlea.

Figure 3A:
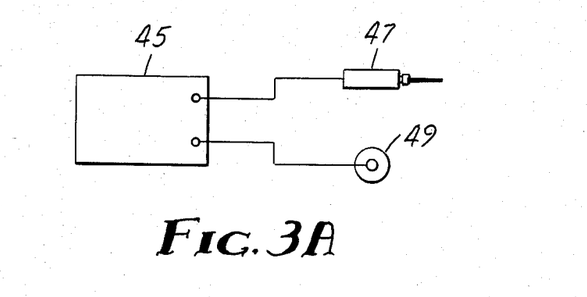
FIGS. 3A and 3B are schematic diagrams of the testing apparatus according to the present invention.

The apparatus schematically illustrated in FIG. 3A comprises means for stimulating the inner ear with an electrical signal having two or more sequential pulses with a predetermined amplitude and a predetermined time delay therebetween. Typically the stimulation means includes a constant current pulse generator 45 which is capable of selectively producing a series of A-C coupled, biphasic or monophasic pulses in the range of 10 microamps to 10 milliamps, with a typical pulse width of 100 microseconds, and with a repetition rate of from 200 to 15,000 pulses per second. The generator 45 should be electrically isolated from ground and preferably have a AC time constant of not more than 10 seconds and a settling time to 0.01 percent in less than 50 microseconds. The pulse generator is coupled to a first electrode 47 which is placed adjacent to the inner ear of the patient being tested. Typically this first electrode 47 is a needle electrode which is insulated except for the very tip. This needle electrode is inserted by the physician into the middle ear 12 such that it contacts either the round window 27 or the bone surrounding the round window 27. A return electrode 49 to complete the stimulation circuit is typically positioned cutaneously on the scalp of the patient. This return electrode 49 may, however, also be positioned within the middle ear 12. Care should be taken that this return electrode 49 is not proximate any muscular tissue which might also respond to the stimulation signal, and affect the measurement to be made. The electrode 47 (or 49) can either be directly coupled to the pulse generator 45 via a wire or in such cases as with a patient who has already had an electrode or electrodes implanted with his cochlea, e.g. a cochlear implant prothesis, it is possible to use the existing implanted electrode and couple that implanted electrode with RF coupling or other methods of transcutaneous or percutaneous coupling to the generator 45.

Figure 3B:
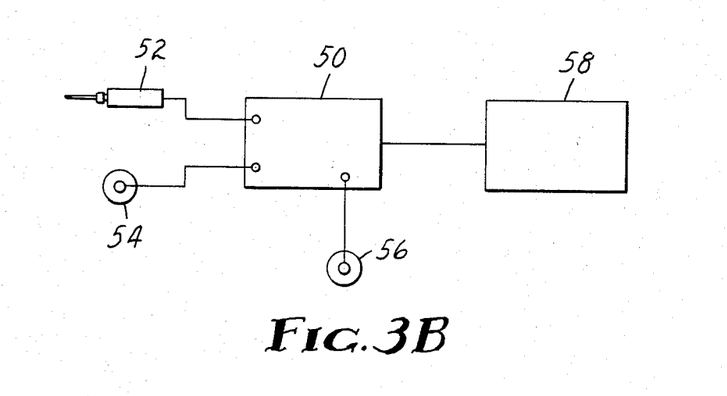

Means, schematically illustrated in FIG. 3B, are provided to sense and compare the resultant electrical activity within the nervous system of the patient being stimulated, which occurs as a response to the electrical stimulation signals. The sensing or measurement means typically include a differential amplifier 50 which amplifies any resulting action potential within the nervous system of the patient. This amplifier typically has a voltage gain of from 1000 to 200,000 over a bandwidth of from 0.1 Hz to 30 kilohertz. The amplifier must be able to recover from an overload to 0.01 percent of the steady state level within 20 microseconds. It should also have an input impedance of greater than or equal to 20 Megohms. It is important that this amplifier 50 be protected from the stimulus signal, as it would be impossible with most amplifiers to recover from such a comparatively large input in an adequate time to meaningfully interpret any comparatively smaller evoked response. This protection for the amplifier 50 can be done with extensive analog and/or digital filtering or with other commercial types of artifact eliminators which are available on the market. If such protection is provided, a bandwidth of 100 Hz to 10 kiloherz is adequate.

The differential amplifier 50 typically has three inputs with which it measures the electrical voltage difference between two sites on or within the patient. Ideally, the positive input of the amplifier 50 is connected to a needle electrode 52 placed within or near the trunk of the auditory nerve 16. The negative input is connected to a second electrode 54 placed at some remote cutaneous location such as on the scalp, and the third input is connected to a reference electrode 56 also generally positioned upon the scalp of the patient.

There are obviously alternate location sites for these electrodes which still afford a measurement of the resulting action potential. For example the positive electrode 52 could be a trans-tympanic needle placed exterior to the inner ear 13 but still adjacent the round window 27. In this case one or both stimulating electrodes may also be utilized as recording electrodes. Similarly, the positive electrode 52 could also be placed in the external ear canal (outer ear 11). Also, the standard brainstem response recording electrode positions could be used. While these alternate locations minimize the complications of entering the inner ear 13, they typically result in a weaker and noisier signal. It is possible, however, to use an averaging processor and repetitive stimulation to extract and measure even these weaker signals from the ever present background noise. In the preferred embodiment a microcomputer 58 is utilized to perform this averaging process on the monitored signal. This microcomputer 58 must be capable of averaging not only individual responses, but the difference between the responses to different stimulus waveforms as well.

The presence of electrical activity within a nerve that has been activated by an electrical stimuli typically results in at least one peak in the electrical voltage signal as measured by the differential amplifier 50, and processed by the microcomputer 58. This peak generally occurs between 0.3 and 0.8 milliseconds after the stimulation signal. In general, several other peaks and with a latency of greater than 0.8 milliseconds follow this first peak. These other peaks typically represent activity in other neurons which have been subsequently activated by the discharge of the auditory nerve fibers. The activity within auditory nerve itself will occasionally give rise to two or three peaks occurring within the same time boundaries noted. These additional peaks represent activity in the auditory nerve fibers, activated by axonal, dendritic and hair cell stimulation. In such cases the existance of dendrites can be inferred directly from the appearance of the additional peaks. Unless the positive recording electrode is positioned directly within the nerve trunk, it is typically not possible to directly resolve more than one peak within the 0.3 to 0.8 millisecond time period. This is probably a result of the distance of the recording electrode 52 from the auditory nerve 16. In such cases it is necessary to further analyze the resulting evoked response in order to provide additional information about the surviving dendrite population. For example, if the peak of an evoked response occurs with a long delay or latency following the stimulus pulse (e.g. 0.5 to 0.7 milliseconds for an extra-trunk electrode) indirect activation of the nerve fibers by the stimulation of the peripheral elements is probably implied. If the peak, however, occurs within a short delay (0.25 to 0.4 milliseconds for the same electrode) direct electrical stimulation of the axon is probably implied. Intermediate delays imply a proportional contribution to the peak by both mechanisms. This method of analysis is, however, ambiguous when latency is measured from a distant (non-invasive) electrode. Thus, an alternate method, as described below is utilized.

As has already been discussed the stimulation signal consists of two or more sequential pulses. Means are therefore included within the present invention for comparing the electrical activity within the nervous system of the patient being stimulated which results from the latter of the two pulses, with the activity resulting from the former or preceding electrical pulse. This is done by subtracting the response due to the first electrical pulse from the response resulting from the pair of electrical pulses. This subtraction results in a difference signal representing only the response due to the second stimulus pulse. (This same process can also be used to determine the response to the last of a sequence of any number of pulses). The size of the peak for this difference signal is then normalized by dividing it by the peak response elicited by the first stimulus pulse. The resulting normalized response magnitude is then plotted as a function of the interpulse interval (IPI). This comparison procedure is performed by a programmed routine within the microcomputer 58, and is the same procedure used in producing the graphs of FIGS. 4 and 5.

The characteristic of importance in interpreting this plot is the ability of the peripheral nerves to fire repeatedly resulting in the monotonicity of the normalized response magnitude for IPI's above 0.3 ms. If excitation occurs only at the auditory nerve axons (i.e., proximal to the cell bodies), a monotonic decline in the response will occur with decreasing (i.e. to 0.3 ms) IPI. However, if surviving dendrites are excited, the relationship of response magnitude to IPI will be non-monotonic. This non-monotonicity may change shape with different stimulus amplitude levels. In particular, the non-monotonicity may be most pronounced at low stimulus amplitudes.

In addition to determining the existance of viable dendrites, the present invention can also be utilized to determine their location. This is because for a given stimulus amplitude, only a specific population of dendrites will exhibit temporal summation when paired stimuli of 0.3 ms IPI are applied. Those which are too far from the stimulus site will not respond even to the paired stimuli. Those which are too close will respond to the first stimulus alone, which response, due to refractoriness, will preclude a response to the second stimulus which immediately follows. Those dendrites which lie between these two spatial boundaries, i.e., within a "subliminal fringe", may respond, but only to the second stimulus. The spatial location of these boundaries along the cochlear spiral varies with stimulus intensity. By increasing the stimulus intensity, the subliminal fringe area may be caused to shift from the basal or proximate end to the apical or distal end of the cochlea. Only surviving dendrites which lie within the fringe will contribute to the second response at the corresponding stimulus intensity. The location of the surviving dendrites can thus be mapped within the cochlea by identifying those stimulus intensities where temporal summation is found. The corresponding fringe areas must contain viable dendrites.

Additionally this procedure may also be used to determine whether surviving dendrites exist in close proximity to an inserted or implanted electrode or electrodes, such as would be the case with a patient already having a cochlear implant.

Having thus described the research and results leading to the present invention, it can be understood that the methods and apparatus taught herein afford a diagnostic procedure for determining the location and viability of dendrites, in a manner which is also minimally invasive. It will also be understood that changes may be made in the size, shape, and configuration of the apparatus, and in the order and particular parameters of the method steps without departing from the present invention as recited in the appended claims.

What is claimed is:

1. A method of diagnosing the extent of survival of the peripheral sensori-neural elements with a patient, comprising the steps of:

stimulating the inner ear of the patient with a first electrical stimulus signal and a second electrical stimulus signal having a first predetermined delay with respect to said first electrical stimulus signal;

measuring the electrical activity within the nervous system of the patient which results from said first electrical stimulus signal and said second electrical stimulus signal having a first predetermined delays then stimulating the inner ear of the patient with said first electrical stimulus signal and said second electrical stimsulus signal having a second predetermined delay with respect to said first electrical stimulus signal;

measuring the electrical activity within the nervous system of the patient which results from said first electrical stimulus signal and said second electrical stimulus signal having a second predetermined delay; and comparing the electrical activity within the nervous system of the patient which results from said first and second electrical stimulus signals with said first predetermined delay with the electrical activity within the nervous system of the patient which results from said first and second electrical stimulus signal with said second predetermined delay.

2. The according to claim 1 wherein said stimulation of the inner ear with a first or a second electrical stimulus signal comprises implanting an active electrode adjacent to or within the inner ear of the patient, generating a constant current pulse having a predetermined amplitude and a predetermined duration, and conveying said constant current pulse to said active electrode thereby stimulating the inner ear.

3. The method according to claim 1 further comprising normalizing the electrical activity within the nervous system of the patient which results from the second electrical stimulus signal by the electrical activity within the nervous system which results from the first electrical stimulus signal, and determining the normalized electrical activity which results from said second stimulus signal as a function of the inter signal delay.

4. The method according to claim 2 further comprising placing a return electrode in electrical contact with the skin of the patient.

5. The method according to claim 2 further comprising implanting a return electrode adjacent to or within the inner ear but remote from the active electrode.

6. The method according to claim 1 wherein said measuring of electrical activity with the nervous system comprises implanting a first electrode adjacent to or within the auditory nerve and placing a second electrode in electrical contact with the skin of the patient.

7. A method as in claim 1 wherein said predetermined delays are varied to occur on either side of the absolute refractory.

8. An apparatus for determining the viability of peripheral sensori-neural elements within a cochlea of a patient, comprising: means for stimulating the inner ear of the patient with a first electrical stimulus signal and a second electrical stimulus signal having a first predetermined delay with respect to said first electrical stimulus signal;

means for measuring the electrical activity within the nervous system of the patient which results from said first electrical stimulus signal and said second electrical stimulus signal having a first predetermined delay;

means for stimulating the inner ear of the patient with said first electrical stimulus signal and said second electrical stimulus signal having a second predetermined delay with respect to said first electrical stimulus signal;

means for measuring the electrical activity within the nervous system of the patient which results from said first electrical stimulus signal and said second electrical stimulus signal having a second predetermined delay; and means for comparing the electrical activity within the nervous system of the patient which results from said first and second electrical stimulus signal with said first predetermined delay with the electrical activity within the nervous system of the patient which results from said first and second electrical stimulus signal with said second predetermined delay.

9. An apparatus as claimed in claim 8 wherein said means for stimulating the inner ear comprises a first electrode adapted to be implanted adjacent the round window of the patient's inner ear;

means for generating a first electrical pulse having a predetermined amplitude and a predetermined duration;

means for generating a second electrical pulse having a predetermined amplitude, a predetermined duration, and a predetermined delay with respect to the first electrical siganl; and means for conveying said electrical pulses to said first electrode.

10. An apparatus as claimed in claim 8 wherein said means for measuring the electrical activity which occurs as a result of said electrical stimulus signals comprises a first electrode implanted adjacent to or within the auditory nerve and a second electrode placed in electrical contact with the skin of the patient.

11. An apparatus as claimed in claim 8 further comprising means for normalizing the electrical activity resulting from said second electrical signal by the electrical activity resulting from said first electrical signal, and means for determining the normalized electrical activity resulting from said second electrical signal as a function of the inter signal delay.

12. An apparatus as claimed in claim 8 further comprising a second electrode adapted to be placed cutaneously on the patient.

13. An apparatus as claimed in claim 9 further comprising a second electrode also adapted to be implanted adjacent the round window of the inner ear but remotely from said first electrode and coupled to said means for conveying.

14. An apparatus as in claim 8 wherein said predetermined delays are varied to occur on either side of the absolute refractory.

15. A method of diagnosing the extent of survival of the peripheral sensori-neural elements within a patient, comprising the steps of:

stimulating the inner ear of the patient with a first electrical stimulus signal;

measuring the electrical activity within the nervous system of the patient which results from said first electrical stimulus signal;

stimulating the inner ear of the patient with a second electrical stimulus signal and a third electrical stimulus signal having a first predetermined delay with respect to said second electrical stimulus signal;

measuring the electrical activity within the nervous system of the patient which results from said second electrical stimulus signal and said third electrical stimulus signal;

subtracting the measured electrical activity within the nervous system which results from said first electrical stimulus signal from the measured electrical activity within the nervous system of the patient which results from said second and third electrical stimulus signals;

stimulating the inner ear of the patient with a fourth electrical stimulus signal and a fifth electrical stimulus signal having a second predetermined delay with respect to said fourth electrical stimulus signal;

measuring the electrical activity within the nervous system of the patient which results from said fourth electrical stimulus signal and said fifth electrical stimulus signal;

subtracting the electrical activity within the nervous system of the patient which results from said first electrical stimulus signal from the measured electrical activity within the nervous system of the patient which results from said fourth and fifth electrical stimulus signals; and comparing the electrical activity within the nervous system of the patient resulting from said first subtraction with the electrical activity within the nervous system of the patient which results from said second subtraction.

* * * * *

UNITED STATES PATENT AND TRADEMARK OFFICE
CERTIFICATE OF CORRECTION

PATENT NO. : 4,535,785

DATED : August 20, 1985

INVENTOR(S) : Christopher van den Honert and Paul H. Stypulkowski

It is certified that error appears in the above-identified patent and that said Letters Patent is hereby corrected as shown below:

Col. 1, line 3, "SENSORI-NEUTRAL" should read --SENSORI-NEURAL--.
Col. 2, line 49, "denritic" should read --dendritic--.
Col. 2, line 56, "patients" should read --patient's--.
Col. 2, line 61, "viz" should read --via--.
Col. 3, line 41, "existance" should read --existence--.
Col. 4, line 50, "dependant" should read --dependent--.
Col. 7, line 55, "ototxic" should read --ototoxic--.
Col. 11, line 14, "delays" should read --delay--.
Col. 11, line 32, --method-- should be inserted after "The".

Signed and Sealed this

Eleventh Day of February 1986

[SEAL]

Attest:

DONALD J. QUIGG

Attesting Officer

Commissioner of Patents and Trademarks